(12) United States Patent
Elliott et al.

(10) Patent No.: US 10,893,910 B2
(45) Date of Patent: *Jan. 19, 2021

(54) SPINAL IMPLANT SYSTEM AND METHOD

(71) Applicant: Warsaw Orthopedic, Inc., Warsaw, IN (US)

(72) Inventors: John A. Elliott, Atoka, TN (US); Julien J. Prevost, Memphis, TN (US); Daniel Paxton Wall, Cordova, TN (US); Mark R. Grizzard, Munford, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 4 days.

This patent is subject to a terminal disclaimer.

(21) Appl. No.: 16/163,666

(22) Filed: Oct. 18, 2018

(65) Prior Publication Data
US 2020/0121397 A1 Apr. 23, 2020

(51) Int. Cl.
| | |
|---|---|
| *A61B 17/88* | (2006.01) |
| *A61B 34/20* | (2016.01) |
| *A61B 34/30* | (2016.01) |
| *A61B 17/70* | (2006.01) |
| *A61B 90/00* | (2016.01) |
| *A61B 17/00* | (2006.01) |

(52) U.S. Cl.
CPC .......... *A61B 34/20* (2016.02); *A61B 17/7074* (2013.01); *A61B 34/30* (2016.02); *A61B 90/361* (2016.02); *A61B 17/00234* (2013.01); *A61B 2017/00477* (2013.01); *A61B 2034/2051* (2016.02); *A61B 2034/2055* (2016.02); *A61B 2034/303* (2016.02); *A61B 2034/305* (2016.02)

(58) Field of Classification Search
CPC ....... A61B 34/20; A61B 34/30; A61B 90/361; A61B 17/7074; A61B 17/7076; A61B 17/708; A61B 17/7082; A61B 17/7085; A61B 17/7091; A61B 17/00234; A61B 2034/2051; A61B 2034/2055; A61B 2034/303; A61B 2034/305; A61B 2017/00477
USPC ....... 606/246, 270, 279, 301, 305, 306, 308, 606/323, 92–94, 97, 99, 102, 104, 86 A
See application file for complete search history.

(56) References Cited

U.S. PATENT DOCUMENTS

| | | | | |
|---|---|---|---|---|
| 2007/0233079 | A1* | 10/2007 | Fallin | A61B 17/7085 606/86 A |
| 2008/0065083 | A1* | 3/2008 | Truckai | A61B 17/3472 600/407 |
| 2011/0130761 | A1* | 6/2011 | Plaskos | A61B 17/155 606/87 |
| 2011/0313281 | A1* | 12/2011 | Grinberg | A61B 17/16 600/424 |

(Continued)

*Primary Examiner* — Eduardo C Robert
*Assistant Examiner* — David C Comstock
(74) *Attorney, Agent, or Firm* — Sorell, Lenna & Schmidt, LLP

(57) ABSTRACT

A surgical instrument comprises a first member including a drive engageable with a first mating surface of a bone fastener. A second member is rotatable relative to the first member and includes an engagement element connectable with a second mating surface of the bone fastener. A part is disposed with the first member and being alternately connectable with an actuator and an adaptor attachable with an image guide. Systems, surgical adaptors, spinal implants and methods are disclosed.

19 Claims, 18 Drawing Sheets

(56) References Cited

U.S. PATENT DOCUMENTS

| | | | |
|---|---|---|---|
| 2012/0203288 A1* | 8/2012 | Lange | A61B 17/7082 606/305 |
| 2015/0150683 A1* | 6/2015 | Donner | A61B 17/88 623/16.11 |
| 2015/0282855 A1* | 10/2015 | Bess | A61B 17/8875 606/86 A |
| 2016/0066957 A1* | 3/2016 | Biedermann | A61B 17/7076 606/272 |
| 2017/0258535 A1* | 9/2017 | Crawford | A61B 17/7074 |
| 2018/0344301 A1* | 12/2018 | Wehrli | A61B 17/00 |
| 2018/0368924 A1* | 12/2018 | Pandya | A61B 17/1764 |
| 2019/0380748 A1* | 12/2019 | Doose | A61B 17/7082 |

* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument comprises a first member including a drive engageable with a first mating surface of a bone fastener. A second member is rotatable relative to the first member and includes an engagement element connectable with a second mating surface of the bone fastener. A part is disposed with the first member and is alternately connectable with an actuator and an adaptor attachable with an image guide. In some embodiments, systems, surgical adaptors, spinal implants and methods are disclosed.

In one embodiment, a spinal implant system is provided. The spinal implant system comprises a surgical instrument including an outer sleeve having a drive engageable with a bone fastener shaft, and an inner sleeve being rotatable relative to the outer sleeve and including an element connectable with a threaded surface of a bone fastener receiver. A part is disposed with the outer sleeve. A removable handle is connectable with the part and engageable with the inner sleeve for rotation therewith. An adaptor is connectable with the part. An image guide is attachable with the adaptor and oriented relative to a sensor to communicate a signal representative of a position of the surgical instrument.

In one embodiment, the surgical system comprises a surgical instrument including an outer sleeve having a drive engageable with a bone fastener shaft, and an inner sleeve being rotatable relative to the outer sleeve and including an element connectable with a threaded surface of a bone fastener receiver. A part is disposed with the first member and alternately connectable with an actuator and an adaptor. A guide member includes an inner surface that defines a cavity configured for disposal of the outer sleeve. An image guide is attachable with the adaptor and being oriented relative to a sensor to communicate a signal representative of a position of the guide member.

BRIEF DESCRIPTION OF THE DRAWINGS

The present disclosure will become more readily apparent from the specific description accompanied by the following drawings, in which.

DETAILED DESCRIPTION

Figure 1:
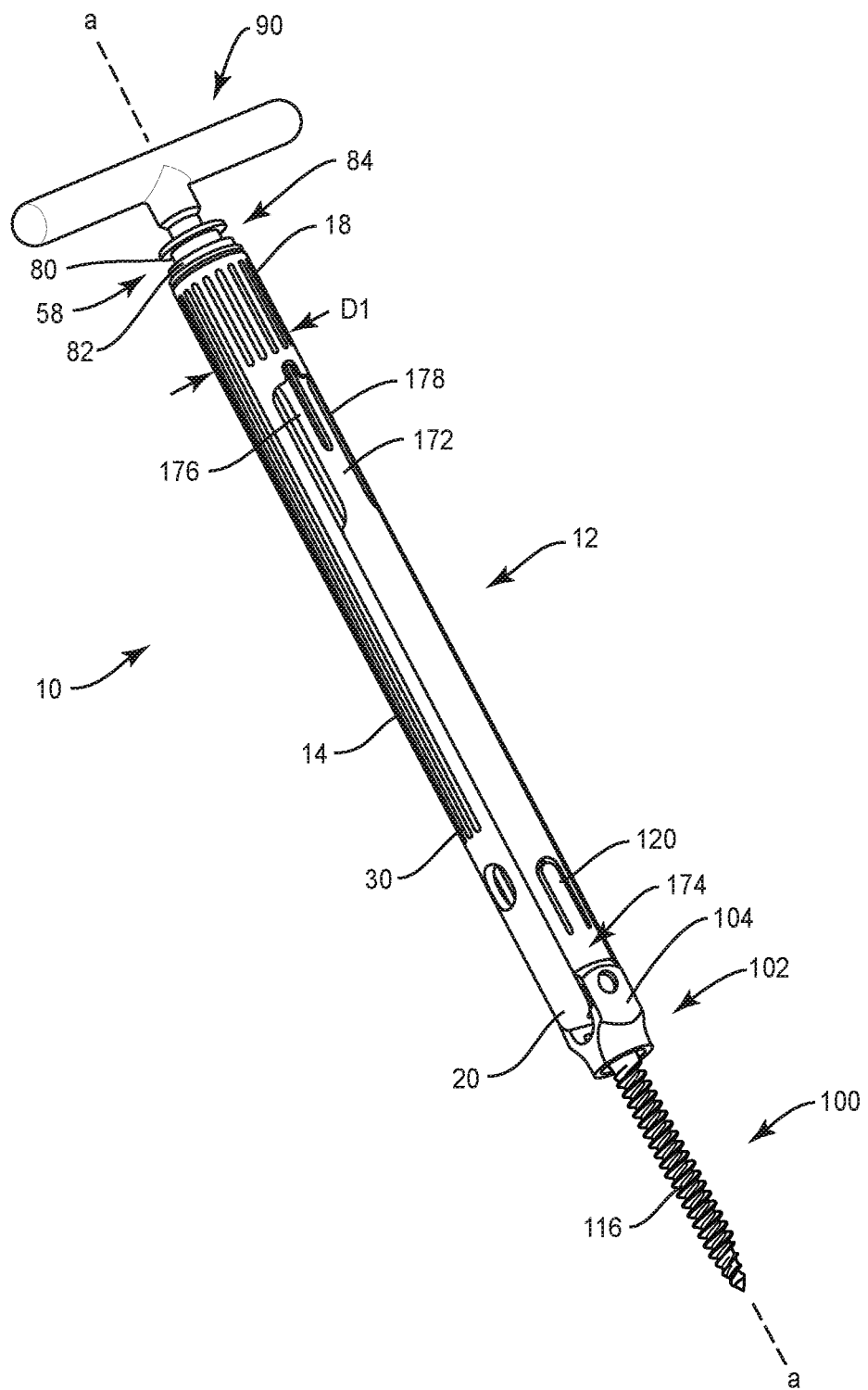
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument that comprises a sleeveless surgically navigated driver. In some embodiments, the present surgical system comprises a surgical instrument that comprises a sleeveless surgically navigated driver employed with a surgical robotic guidance system. In some embodiments, the driver can be connected with extended tabs of a bone screw. In some embodiments, the driver can be connected with a break-away adapter. In some embodiments, the driver can be connected with fenestrated screws connectable with bone filler device (BFD) attachments. In some embodiments, the driver can be employed with a bone screw that provides bi-cortical fixation to enhance fixation with vertebrae and reduce the risk of screw loosening when used with a biologic or agent, for example, bone cement (PMMA), and/or reduce the risk of biologic or agent leakage outside of a vertebral body.

In some embodiments, the present surgical system comprises a surgical instrument that comprises a screw driver. In some embodiments, the driver is configured for use with a spinal implant, such as, for example, a bone fastener or screw. The bone fastener may include open tulip head receivers and/or closed tulip head receivers. In some embodiments, the driver can be employed with a posted screw, a pedicle screw, a bolt, a bone screw for a lateral plate, a uni-axial screw (URS), a fixed angle screw (FAS), a multi-axial screw (MAS), a side loading screw, a sagittal adjusting screw (SAS), a transverse sagittal adjusting screw (TSAS), an awl tip (ATS) or a sacral bone screw.

In some embodiments, the present surgical system comprises a surgical driver instrument that comprises an internal thread to align/tighten a bone screw to the driver. In some embodiments, the driver employs a navigated break away adapter that provides a shortened over-all length of the driver and streamlines multiple-screw placement. In some embodiments, the driver includes a tip configured to mate with ATS, MAS, and SAS fenestrated screws. In some embodiments, the present surgical system comprises a surgical driver instrument employed with a handle. In some embodiments, the handle can be employed to tighten/align bone screws with the driver. In some embodiments, the handle can be used as a punch configured to displace material, for example, cement, which may become trapped in the driver tip.

In some embodiments, the present surgical system comprises a surgical driver instrument that includes an internal thread capture of a receiver of a bone screw. In some embodiments, the present surgical system comprises a surgical driver instrument that is engageable with driver tips for ATS, MAS and SAS bone screws. In some embodiments, the surgical driver instrument comprises a removable handle configured to tighten/align a screw to the driver. In some embodiments, the handle includes a tip configured as a punch that avoids cement overflow for fenestrated screws.

In some embodiments, the present surgical system comprises a surgical instrument that comprises a screw driver with a disengagement feature. In some embodiments, the driver is configured for use with a spinal implant, such as, for example, a bone fastener. The bone fastener may include open tulip head receivers and/or closed tulip head receivers. In some embodiments, the driver includes an inner thread to retain the bone fastener with the driver. In some embodiments, the screw driver is employed with robotic guidance. In some embodiments, the driver includes an inner shaft having a Torx tip configured for engagement with the bone fastener.

In some embodiments, the present surgical system comprises a surgical instrument that comprises a screw driver that can be employed with bone fasteners and one or more implant supports for treating a spine. In some embodiments, the present surgical system includes a surgical instrument that can easily connect and disconnect from a bone fastener. In some embodiments, the present surgical system includes a surgical instrument that can be employed with an end effector of a robotic arm to facilitate implant with the robotic arm. In some embodiments, the surgical instrument is guided through the end effector for a guide-wireless screw insertion. In some embodiments, the surgical instrument comprises a robot screw driver employed with robotic and/or navigation guidance, which may include an image guide.

In some embodiments, the present surgical system includes a screw driver having an outer shaft and a drive tip that engages a bone fastener. In some embodiments, the outer shaft and the drive tip are of one piece construction. In some embodiments, the one piece construction allows tolerances to be controlled tightly for improved accuracy of trajectory during implant insertion. In some embodiments, the drive tip includes a Torx configuration. In some embodiments, the present surgical system includes a screw driver having an internal retention mechanism. In some embodiments, the retention mechanism is fixed with a receiver of a bone fastener to resist and/or prevent disengagement of the retention mechanism from the receiver, for example, due to connection or friction with the end effector or tissue.

In some embodiments, the present surgical system includes a screw driver for use with robotic surgery. In some embodiments, the screw driver can be employed with FAS, IFAS, SAS, TSAS and MAS, and allows the screws to be driven through a robotic end effector. In some embodiments, the screw driver includes a one piece outer sleeve having a tip. In some embodiments, the screw driver includes an internal retaining device that prevents accidental disengagement and/or unthreading.

In some embodiments, the present surgical system includes a screw driver including an outer shaft or sleeve having an outside diameter that is slightly larger than a screw spin diameter of a bone screw. This configuration allows the bone screw and the screw driver to pass through the end effector. In some embodiments, the screw driver includes a handle that is connected to a retention screw that threads into the bone screw. In some embodiments, the present surgical system includes tab extenders connected to the screw driver and prevented from extending outside the outside diameter of the screw driver by engaging undercuts of the screw driver. This configuration prevents an interference or hang-up if the bone screw needs to be removed through the end effector.

In some embodiments, the screw driver is configured for connection with a bone filler device. In some embodiments, the screw driver is cannulated. In some embodiments, connection of the bone filler device allows for injection of bone cement without removal of the screw driver. In some embodiments, the navigation component of the driver can facilitate determination of screw placement for disposal of bone cement therewith. In some embodiments, the navigation component can provide a secondary confirmation to check screw placement, driver trajectory and/or assess if a three dimensional navigation component spin has been compromised.

In some embodiments, the screw driver is connected with the adaptor. In some embodiments, the screw driver is connected with the navigation component by a flange of the screw driver. In some embodiments, the adaptor and the navigation component provide for navigation and torque. In some embodiments, the adaptor and navigation component are removed from the driver after a bone fastener is engaged with tissue. In some embodiments, the bone filler device is engaged with the flange of the screw driver and a shaft of the bone filler device is disposed through the screw driver. In some embodiments, the bone filler device injects cement into the bone fastener through the screw driver.

In some embodiments, the surgical system includes a handle configured as a hex key. In some embodiments, the hex key is configured to lock and/or unlock the driver. In some embodiments, the hex key includes an extension sized for disposal with a cannulated portion of the driver tip. In some embodiments, the extension is configured to punch and/or dislodge bone cement that may have leaked inside the cannulated portion of the driver tip. In some embodiments, the extension is configured to facilitate removal of bone cement from the cannulated portion.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise, Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-13, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 10 includes a surgical instrument, such as, for example, a driver 12. Driver 12 can be employed with a guide member, such as, for example, an end effector 200 (FIGS. 8, 9, 11 and 12) of a robotic arm R (FIG. 13) to facilitate implant with robotic arm R. Driver 12 is guided through end effector 200 for guide-wireless insertion of a spinal implant, such as, for example, a bone fastener 100, as described herein. See also, the examples and disclosure of surgical instruments, spinal implant systems and methods shown and described in commonly owned and assigned U.S. patent application Ser. No. 16/163,668 filed Oct. 18, 2018, and published as U.S. Patent Application Publication No. 2020/0121398, on Apr. 23, 2020, the entire contents of which being incorporated herein by reference.

Driver 12 includes a member, such as, for example, a tubular outer sleeve 14. Outer sleeve 14 extends between a proximal end 18 and a distal end 20. Outer sleeve 14 defines a longitudinal axis a. In some embodiments, outer sleeve 14 may have various configurations including, for example, round, oval, polygonal, irregular, consistent, variable, uniform and non-uniform. Outer sleeve 14 includes a diameter D1. In some embodiments, diameter D1 is slightly larger than a screw spin diameter D2 of bone fastener 100. This configuration allows bone fastener 100 and driver 12 to pass through end effector 200 of robotic arm R, as described herein.

Outer sleeve 14 includes a surface 50 that defines a channel 52. Channel 52 is configured for disposal of a member, such as, for example, an inner shaft 56 and an engagement element, such as, for example, a screw 64, as described herein. Driver 12 includes a part 58 disposed with sleeve 14. Part 58 is alternately connectable with an actuator and an adaptor attachable with an image guide, as described herein. Part 58 has a flange 80 and a flange 82 that is spaced apart from flange 80 by a recess 84. Part 58 has a surface 86 that defines a cavity 88 alternately configured for disposal of an actuator, such as, for example, a removable handle 90 therein and an adaptor, such as, for example, an adaptor 250 therein. See also, the examples and disclosure of surgical instrument adaptors, spinal implant systems and methods shown and described in commonly owned and assigned U.S. patent application Ser. No. 16/163,645 filed Oct. 18, 2018, and published as U.S. Patent Application Publication No. 2020/0121396, on Apr. 23, 2020, the entire contents of which being incorporated herein by reference. Cavity 88 is in alignment with channel 52 to facilitate insertion of inner shaft 56 into end 18, through part 58 and into channel 52 for assembly, as described herein. Handle 90 is configured to actuate rotation of inner shaft 56 and screw 64, as described herein. Handle 90 includes a shaft 92 and a gripping portion 94 that is connected with shaft 92. Shaft 92 extends through part 58 such that shaft 92 is rotatable relative to part 58.

Inner shaft 56 extends between an end 60 and an end 62. End 60 is engageable with shaft 92 for rotation of inner shaft 56 and screw 64, as described herein. Shaft 92 includes a surface 96 that engages a surface 66 of inner shaft 56 in an interference fit to facilitate simultaneous rotation of handle 90 and inner shaft 56. In some embodiments, shaft 92 includes various configurations, such as, for example, hexalobe, cruciform, phillips, square, hexagonal, polygonal, star cross sectional configuration for a mating engagement with correspondingly shaped portion of surface 66. In some embodiments, a distal end of handle 90 includes a punch 98 that is connected with shaft 92. Punch 98 has a maximum diameter that is less than a maximum diameter of shaft 92. Punch 98 is configured to dislodge material, such as, for example, cement that may trapped in a tip of driver 12.

Screw 64 includes an inner surface 68 that defines a cavity 70 configured for disposal of a correspondingly shaped portion of end 62 of inner shaft 56. Surface 68 engages inner shaft 56 in an interference fit to facilitate simultaneous rotation of inner shaft 56 and screw 64, as described herein. In some embodiments, cavity 70 includes various configurations, such as, for example, hexalobe, cruciform, phillips, square, hexagonal, polygonal, star cross sectional configuration for a mating engagement with a correspondingly shaped end 62. Screw 64 includes an outer surface having an engagement element, such as, for example, a thread form 72. Thread form 72 is configured for engagement with a mating surface, such as, for example, thread forms of arms 104, 106 of bone fastener 100 to pull and or draw bone fastener 100 into engagement with driver 12, as described herein.

Inner shaft 56 and screw 64 are configured for movement relative to outer sleeve 14. Screw 64 is inserted laterally into channel 52. Inner shaft 56 is inserted axially into channel 52 such that end 62 is positioned within cavity 70 and surface 68 engages inner shaft 56 in an interference fit. Part 58 is inserted axially into sleeve 14 to connect part 58 with sleeve 14 such that part 58 engages sleeve 14 in an interference fit. Shaft 92 is inserted axially through cavity 88 and into inner shaft 56 such that surface 96 engages surface 66 in an interference fit to facilitate simultaneous rotation of handle 90 and inner shaft 56. Inner shaft 56 retains screw 64 with sleeve 14.

End 20 of outer sleeve 14 includes a distal tip, such as, for example, drive 22. In some embodiments, drive 22 is integrally connected or monolithically formed with outer sleeve 14. This configuration facilitates control of tolerances to optimize accuracy of the connection of outer sleeve 14 with bone fastener 100. In some embodiments, drive 22 is removably connected with outer sleeve 14. Drive 22 is engageable with a spinal implant, such as, for example, bone fastener 100. For example, drive 22 fits with and is engageable with a mating surface, such as, for example, a socket 110 of bone fastener 100. Rotation of outer sleeve 14 simultaneously rotates drive 22 to drive, torque, insert or otherwise connect bone fastener 100 with tissue, as described herein. In some embodiments, drive 22 includes a hexalobe geometry for a mating engagement with a correspondingly shaped socket 110. In some embodiments, drive 22 can alternatively include a cruciform, phillips, square, hexagonal, polygonal, star cross sectional configuration for disposal of a correspondingly shaped socket 110.

Outer sleeve 14 includes an extension 30 and an extension 32. Extensions 30, 32 include a wall 34 having a surface 36. Surface 36 is connectable with an implant support, such as, for example, an extender tab 152, as described herein. Surface 36 defines a mating groove, such as, for example, a pocket 38 configured for engagement with extender tab 152, as described herein. Surface 36 is configured to resist and/or prevent disengagement of extender tab 152 from pocket 38, as described herein.

Extensions 30, 32 include a wall 40 having a surface 42, Surface 42 is connectable with an implant support, such as, for example, an extender tab 152a, as described herein, Surface 42 defines a mating groove, such as, for example, a pocket 44 configured for engagement with extender tab 152a, as described herein. Surface 42 is configured to resist and/or prevent disengagement of extender tab 152a from pocket 44, as described herein.

Pockets 38, 44 are configured for engagement with extender tabs 152, 152a. Disposal of extender tabs 152, 152a with pockets 38, 44 is configured to resist and/or prevent extender tabs 152, 152a from increasing diameter D1 when engaged with driver 12. In some embodiments, pockets 38, 44 are disposed parallel to axis a. In some embodiments, pockets 38, 44 are disposed at alternate orientations relative to axis a, such as, for example, at transverse, perpendicular and/or other angular orientations such as acute or obtuse, and/or may be offset or staggered.

Bone fastener 100 includes a receiver 102. Receiver 102 extends along axis a when connected with outer sleeve 14. Receiver 102 includes arms 104, 106. Arms 104, 106 define an implant cavity configured for disposal of a component of a spinal construct, such as, for example, a spinal rod (not shown). Receiver 102 includes an inner surface having a thread form located adjacent arm 104 and a thread form located adjacent arm 106. The thread forms of arms 104, 106 are configured for engagement with thread form 72 to retain bone fastener 100 with driver 12, as described herein. Bone fastener 100 includes a threaded shaft 116. Shaft 116 is configured to penetrate tissue, such as, for example, bone.

Arm 104 includes a break away tab 120 that is frangibly connected to arm 104 such that manipulation of tab 120 relative to arm 104 can fracture and separate tab 120 from arm 104 at a predetermined force and/or torque limit, as described herein. Arm 106 includes a break away tab 130 that is frangibly connected to arm 106 such that manipulation of tab 130 relative to arm 106 can fracture and separate tab 130 from arm 106 at a predetermined force and/or torque limit, as described herein. In some embodiments, as force and/or torque is applied to tabs 120, 130 and resistance increases, for example, the predetermined torque and force limit is approached.

In some embodiments, tabs 120, 130 can fracture and separate at a predetermined force or torque limit, which may be in a range of approximately 2 Newton meters (N-m) to 8 N-m. In some embodiments, tabs 120, 130 and arms 104, 106 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 120, 130.

Figure 5:
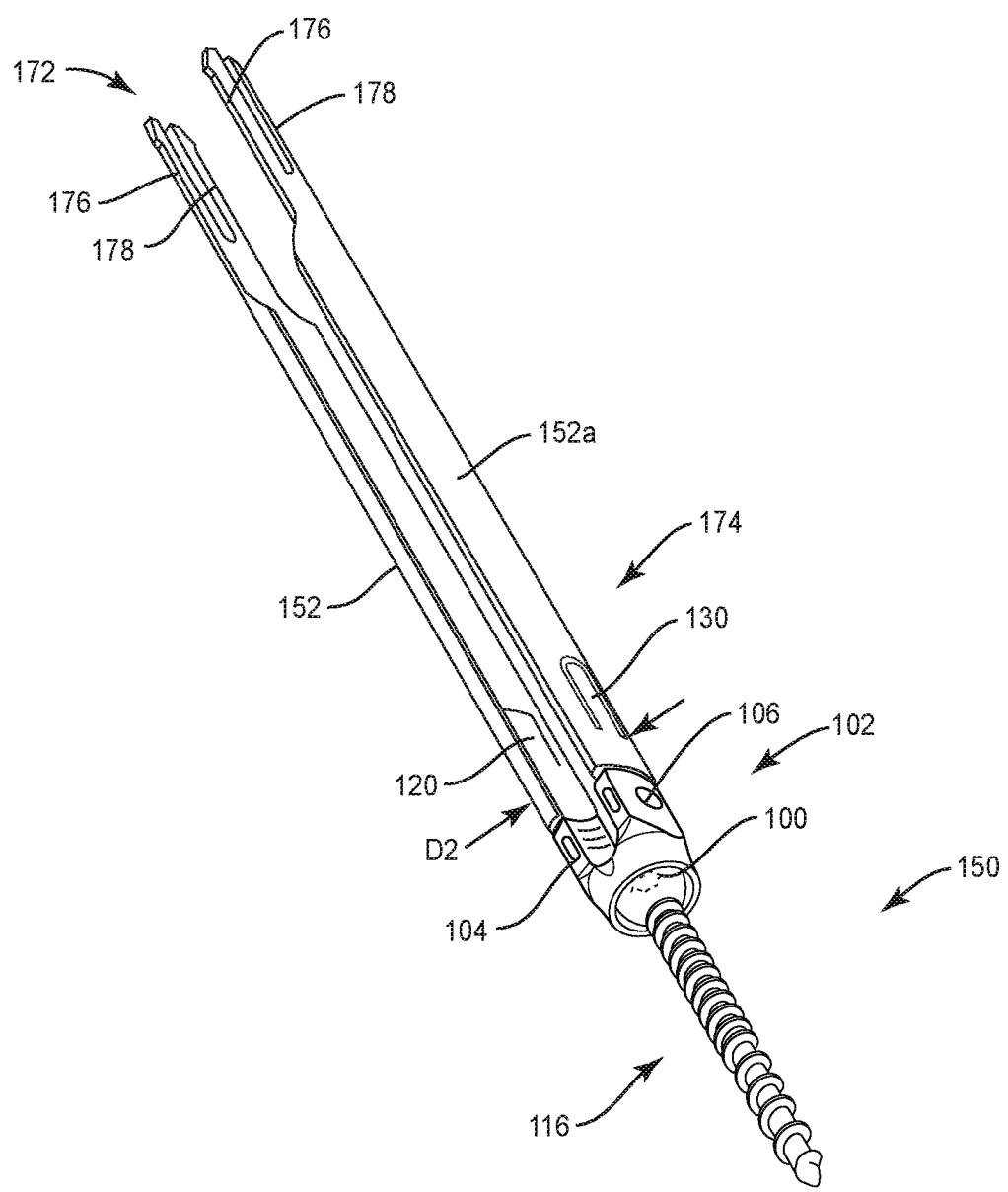
FIG. 5 is a perspective view of components of the surgical system shown in FIG. 1.

A bone fastener assembly 150 includes extender tabs 152, 152a connected with bone fastener 100. Extender tabs 152, 152a extend between a proximal end 172 and a distal end 174. Proximal end 172 includes spring tips 176, 178, as shown in FIG. 5. Spring tips 176, 178 are aligned and disposable with pockets 38, 44. Surfaces 36, 42 are configured to resist and/or prevent disengagement of spring tips 176, 178, as described herein. Distal ends 174 are configured for slidable disposal of a portion of bone fastener 100, such as, for example, tabs 120, 130. In some embodiments, tabs 120, 130 are configured to releasably fix extender tabs 152, 152a with bone fastener 100 for connection with outer sleeve 14.

Figure 2:
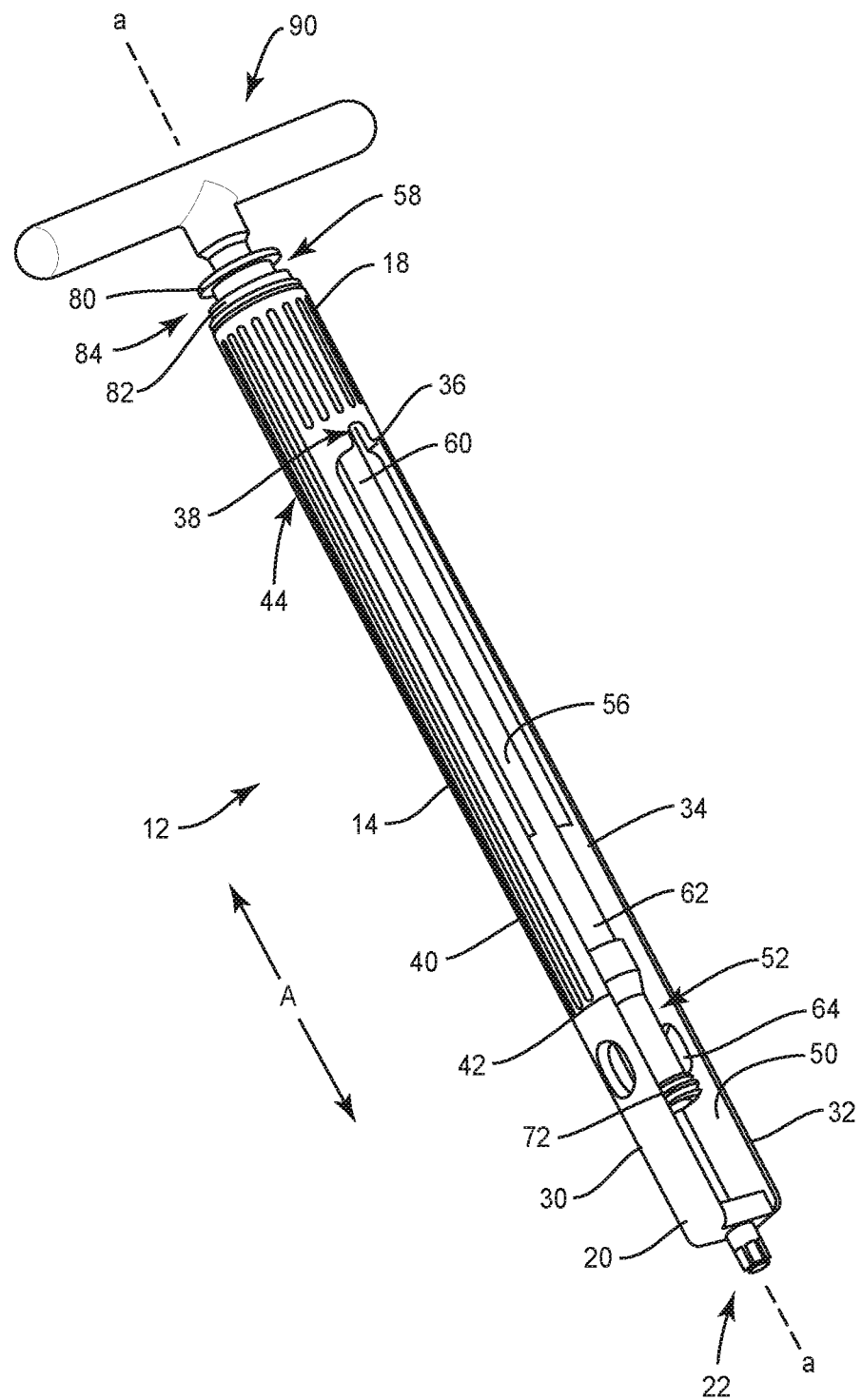
FIG. 2 is a perspective view of components of the surgical system shown in FIG. 1.
Figure 3:
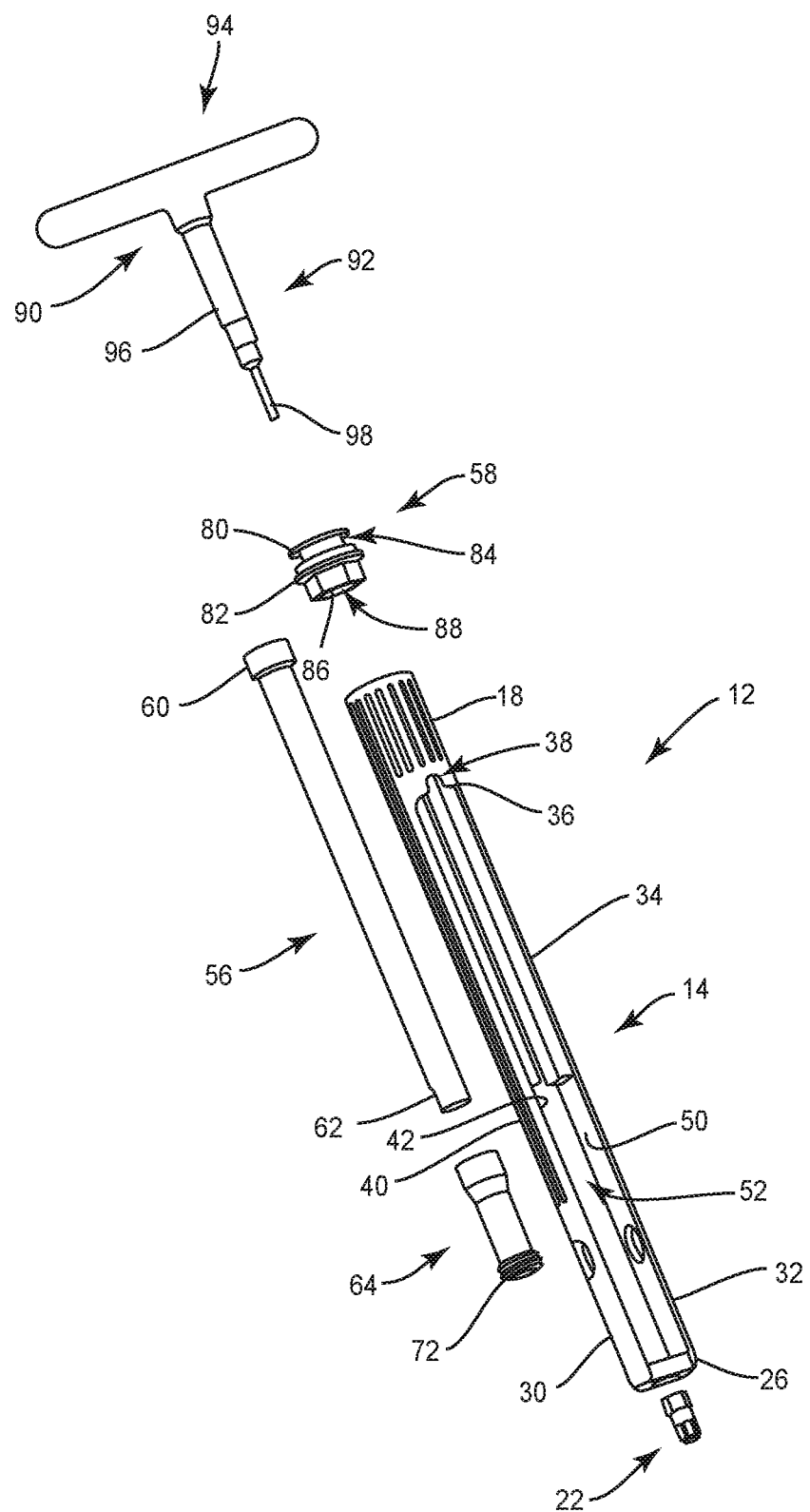
FIG. 3 is a perspective view of the components shown in FIG. 2 with parts separated.
Figure 4:
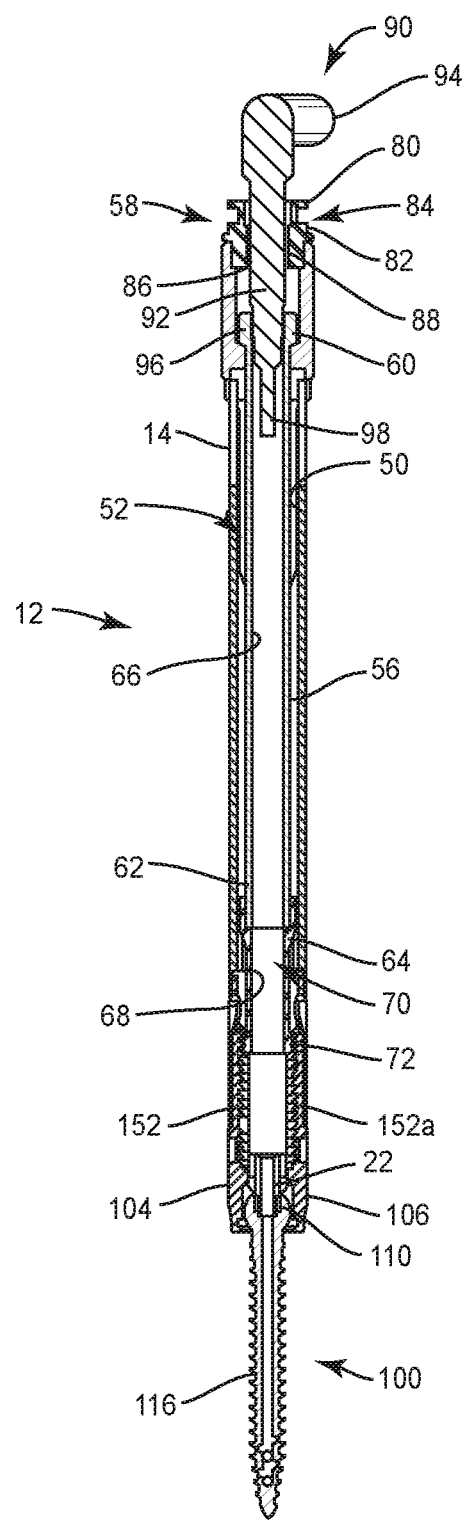
FIG. 4 is a side, cross section view of the components shown in FIG. 1.

In use, bone fastener assembly 150 is connected with driver 12, as described herein, and drive 22 is oriented for engagement with socket 110. Drive 22 is engaged with socket 110 and screw 64 is disposed with inner shaft 56 and assembled with outer sleeve 14 for axial translation relative to outer sleeve 14 and along inner shaft 56 between a non-locking configuration, as shown in FIG. 2, and a locking configuration, as shown in FIG. 4, with a spinal implant, such as, for example, bone fastener 100. In the non-locking configuration, screw 64 is freely translatable relative to inner shaft 56 within channel 52, in the direction shown by arrows A in FIG. 2, and rotatable relative to outer sleeve 14. This configuration allows drive 22 to engage socket 110 prior to fixation of screw 64 with bone fastener 100.

With bone fastener assembly 150 connected with outer sleeve 14, thread form 72 is aligned with the thread forms of arms 104, 106 for engagement therebetween to retain bone fastener 100 with driver 12. Screw 64 is keyed with end 62 for simultaneous rotation with inner shaft 56 and handle 90. Handle 90 is manipulated for rotation such that inner shaft 56 rotates screw 64 relative to and independent of outer sleeve 14. Thread form 72 engages the thread forms of arms 104, 106 and screw 64 axially translates into receiver 102 and relative to inner shaft 56. The threaded engagement of screw 64 and receiver 102 pulls and/or draws bone fastener 100 into the locking configuration with driver 12 for releasable fixation therebetween. Drive 22 is connected with outer sleeve 14, as described herein, and outer sleeve 14 is rotated to drive, torque, insert or otherwise connect bone fastener 100 with adjacent tissue. Screw 64 remains releasably fixed with receiver 102, independent of outer sleeve 14 rotation and/or engagement or friction with components of spinal implant system 10 as described herein, to resist and/or prevent disengagement or unthreading of screw 64 from receiver 102.

Figure 6:
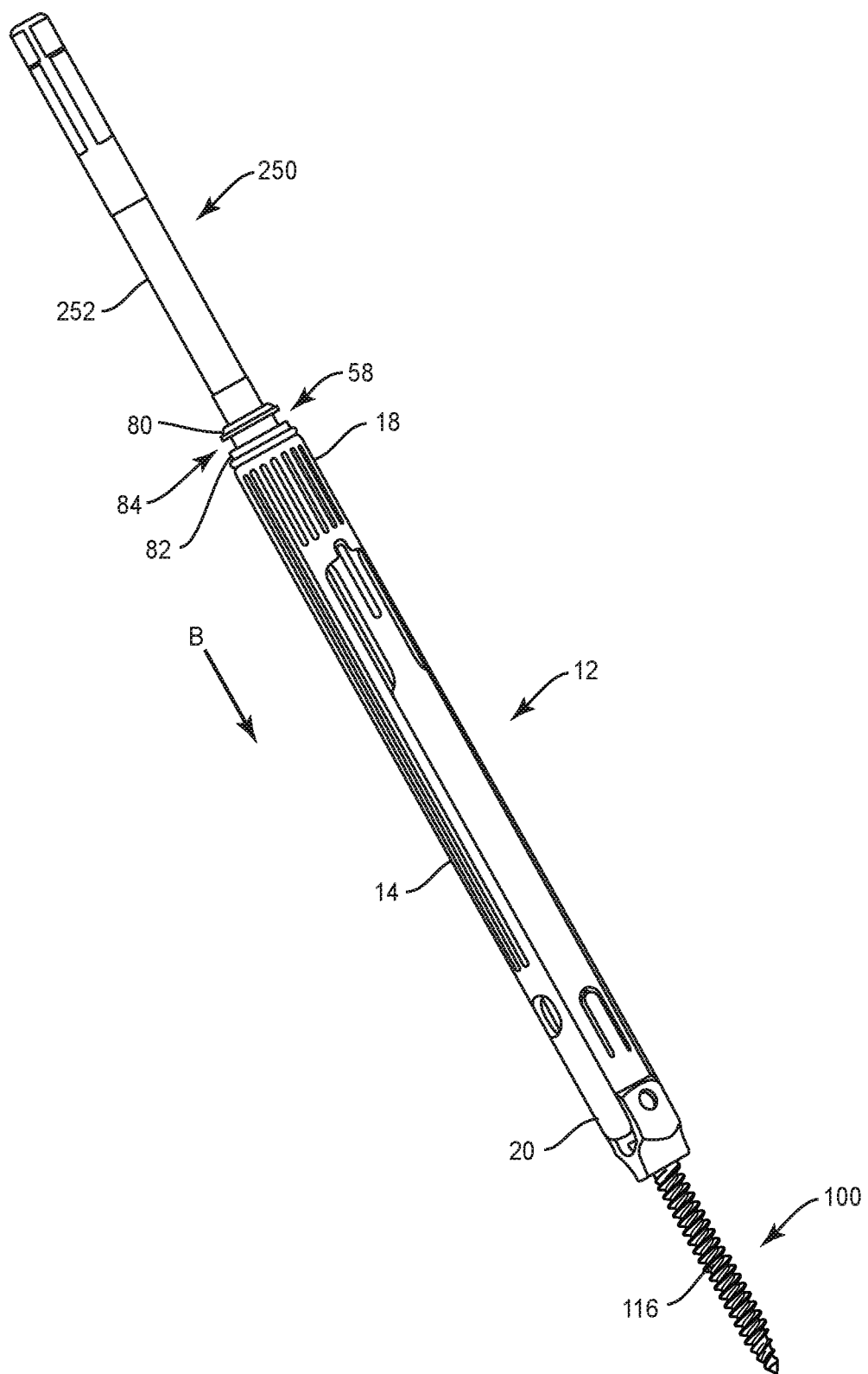
FIG. 6 is a side view of components of one embodiment of a surgical system in accordance with the principles of the present disclosure.
Figure 7:
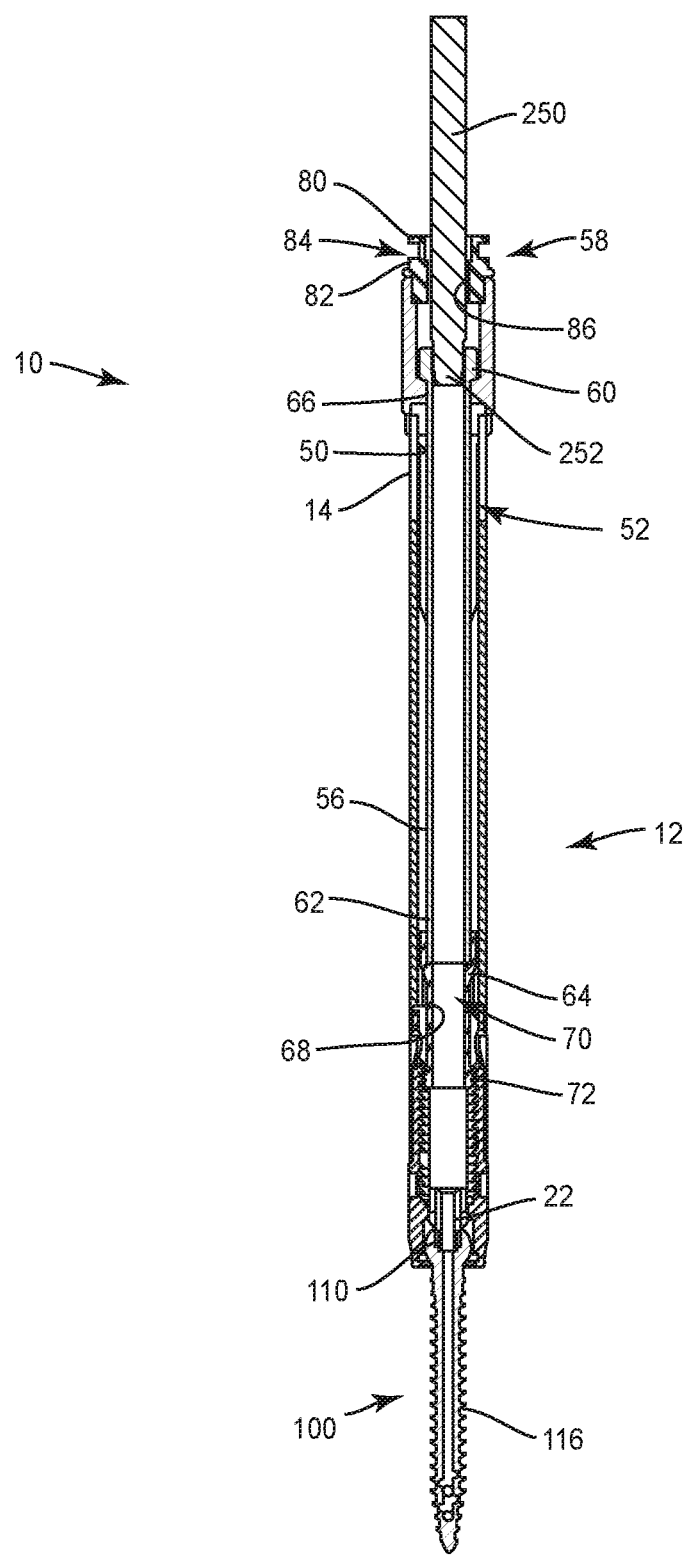
FIG. 7 is a side, cross section view of the components shown in FIG. 6.
Figure 8:
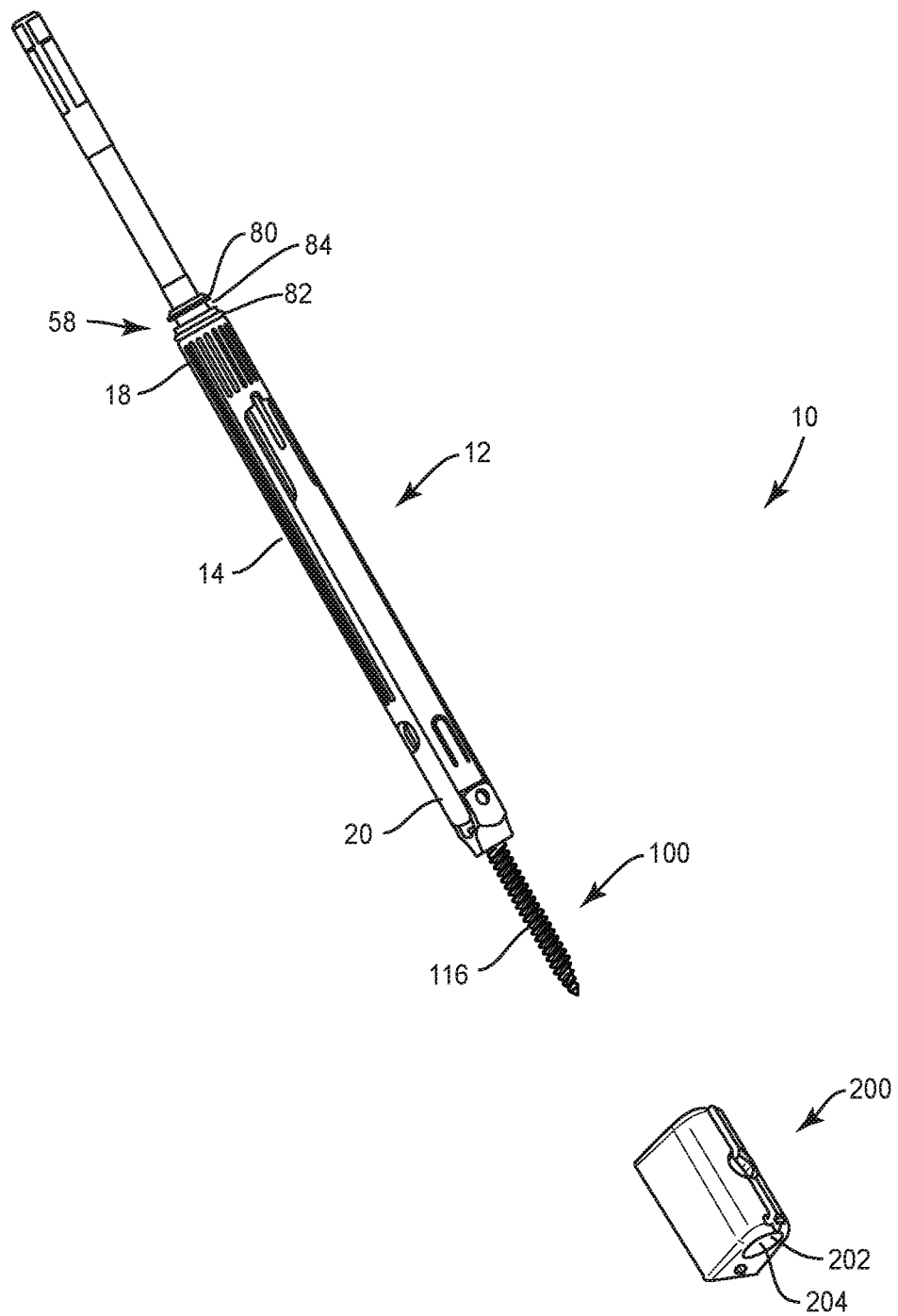
FIG. 8 is a perspective view of components of one embodiment of a surgical system in accordance with the principles of the present disclosure.
Figure 9:
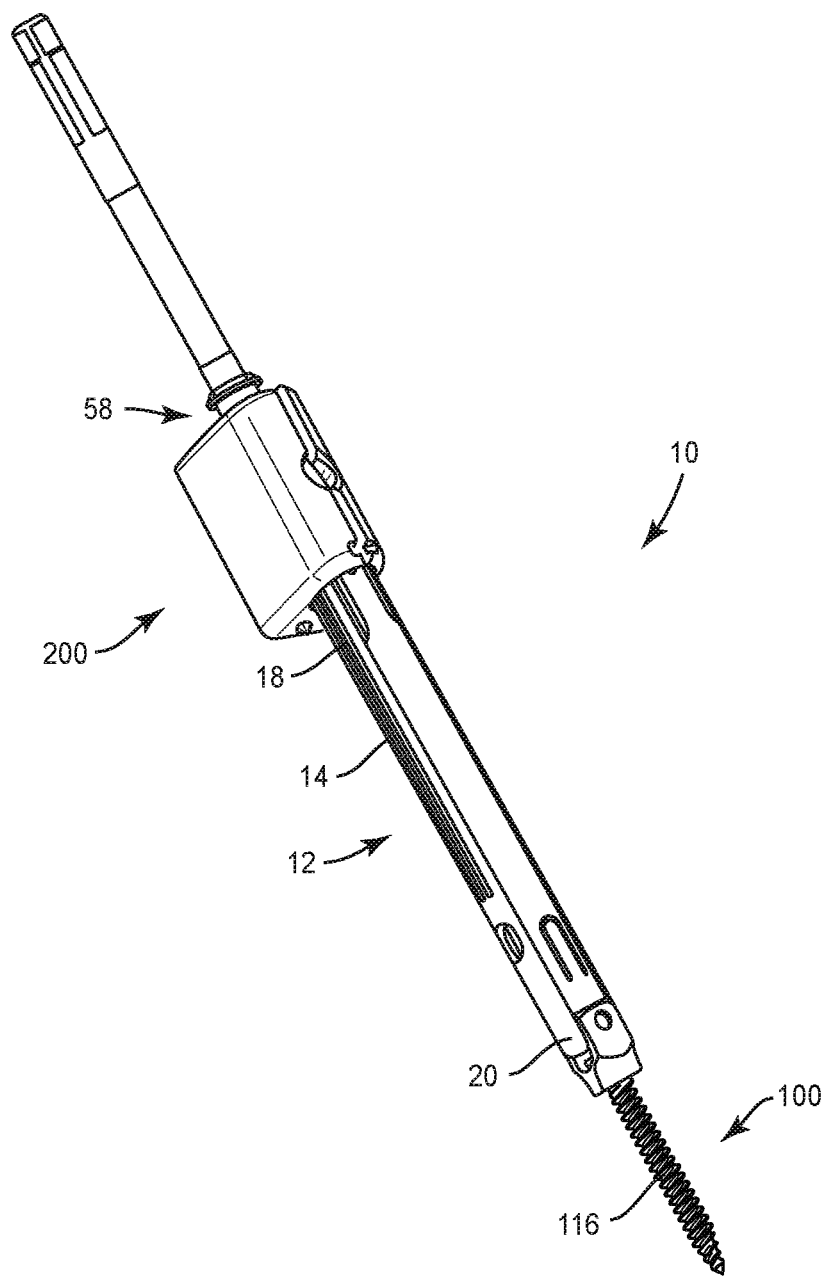
FIG. 9 is a perspective view of the components shown in FIG. 8.

In some embodiments, as shown in FIGS. 6 and 7, handle 90 is removed from inner shaft 56, sleeve 14 and part 58 after screw 64 is moved from the non-locking configuration to the locking configuration and an instrument, such as, for example, adaptor 250 is connected with driver 12 by inserting adaptor 250 through part 58 such that a tip 252 of adaptor 250 is positioned within shaft 56. Adaptor 250 is configured to connect an image guide, such as, for example, a navigation component 300 to driver 12 and/or to connect an actuator, such as, for example, actuator 450 to driver 12, as described herein. Adaptor 250 is fixed relative to shaft 56 and is rotatable relative to part 58. In some embodiments, adaptor 250 is connected to shaft 56 such that adaptor 250 is fixed relative to shaft 56 such that rotation of adaptor 250 also rotates shaft 56. For example, in some embodiments, tip 252 has a polygonal cross sectional configuration, such as, for example, a hexagonal cross sectional configuration and surface 66 of shaft 56 has a polygonal cross sectional configuration, such as, for example, a hexagonal cross sectional configuration that corresponds to the cross sectional configuration of tip 252 such that tip 252 directly engages surface 66 to prevent adaptor 250 from rotating relative to shaft 56.

In some embodiments, driver 12 includes navigation component 300, as shown in FIGS. 10-13. Navigation component 300 is configured to connect to adaptor 250 and part 58 to couple navigation component 300 to driver 12, as discussed herein. Driver 12 is configured for disposal adjacent a surgical site such that navigation component 300 is oriented relative to a sensor array 302 to facilitate communication between navigation component 300 and sensor array 302 during a surgical procedure, as described herein, Navigation component 300 is configured to generate a signal representative of a position of bone fastener 100 relative to driver 12 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, navigation component 300 is connected with adaptor 250 or part 58 via an integral connection, friction fit, pressure fit, interlocking engagement, mating engagement, dovetail connection, clips, barbs, tongue in groove, threaded, magnetic, key/keyslot and/or drill chuck.

Figure 13:
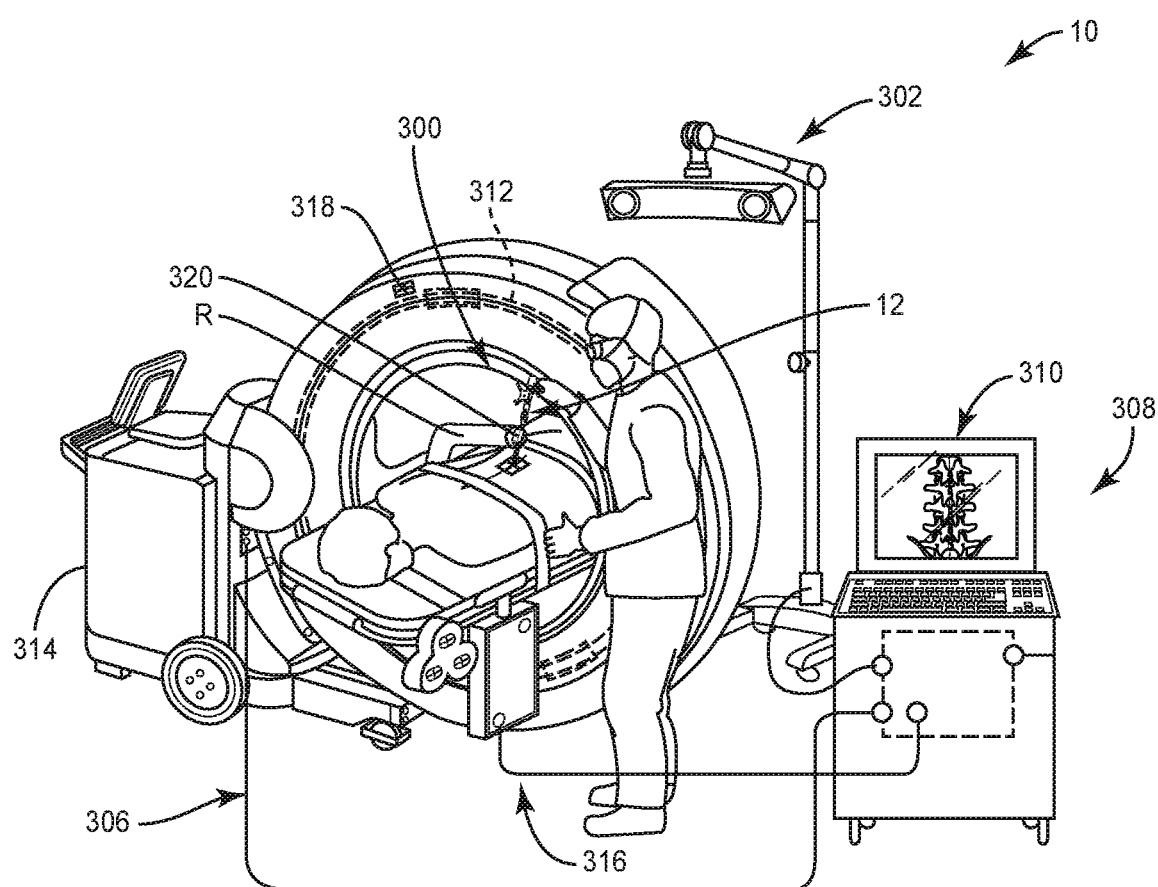
FIG. 13 is a perspective view of components of one embodiment of a surgical system in accordance with the principles of the present disclosure.

Navigation component 300 includes an emitter array 304. Emitter array 304 is configured for generating a signal to sensor array 302 of a surgical navigation system 306, as shown in FIG. 13 and described herein. In some embodiments, the signal generated by emitter array 304 represents a position of bone fastener 100 relative to driver 12 and relative to tissue, such as, for example, bone. In some embodiments, the signal generated by emitter array 304 represents a three dimensional position of bone fastener 100 relative to tissue.

In some embodiments, sensor array 302 receives signals from emitter array 304 to provide a three-dimensional spatial position and/or a trajectory of bone fastener 100 relative to driver 12 and/or tissue. Emitter array 304 communicates with a processor of computer 308 of navigation system 306 to generate data for display of an image on monitor 310, as described herein. In some embodiments, sensor array 302 receives signals from emitter array 304 to provide a visual representation of a position of bone fastener 100 relative to driver 12 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 306 is configured for acquiring and displaying medical imaging, such as, for example, x-ray images appropriate for a given surgical procedure. In some embodiments, pre-acquired images of a patient are collected. In some embodiments, surgical navigation system 306 can include an O-ARM® imaging device 320 sold by Medtronic Navigation, Inc. having a place of business in Louisville, Colo., USA. Imaging device 320 may have a generally annular gantry housing that encloses an image capturing portion 312.

In some embodiments, navigation system 306 comprises an image capturing portion 314 that may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, such as, for example, an optical tracking system that includes an optical localizer, such as, for example, sensor array 302 and/or an EM tracking system that can include an EM localizer. Various tracking devices can be tracked with tracking system 316 and the information can be used by surgical navigation system 306 to allow for a display of a position of an item, such as, for example, a patient tracking device, an imaging device tracking device 318, and an instrument tracking device, such as, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted a computer 314 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of bone fastener 100 relative to driver 12 and/or tissue can be tracked. Sensor array 302 is located in such a manner to provide a clear line of sight with emitter array 304, as described herein. In some embodiments, fiducial markers 330 of emitter array 304 communicate with sensor array 302 via infrared technology. Sensor array 302 is coupled to computer 308, which may be programmed with software modules that analyze signals transmitted by sensor array 302 to determine the position of each object in a detector space.

Figure 10:
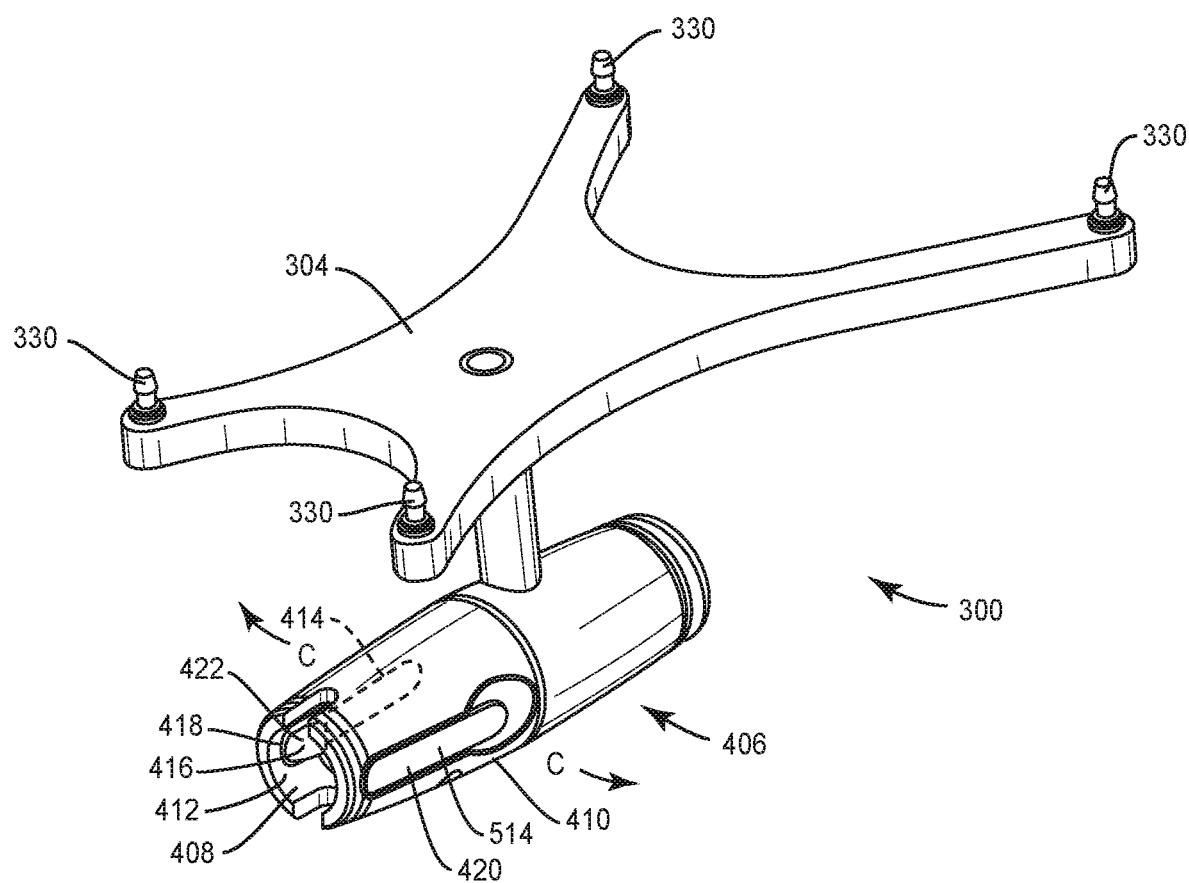
FIG. 10 is a perspective view of one embodiment of components of a surgical system in accordance with the principles of the present disclosure.
Figure 11:
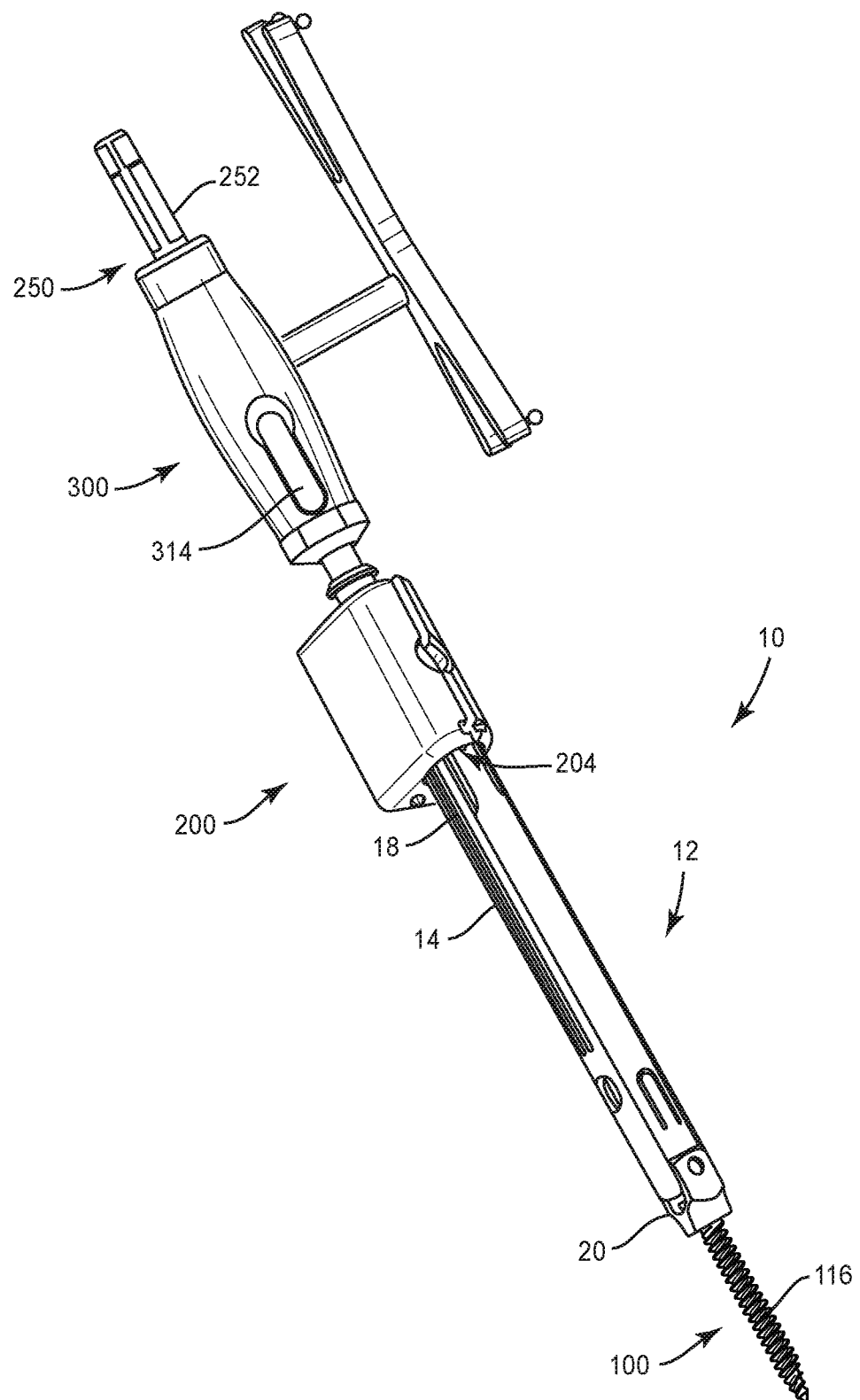
FIG. 11 is a perspective view of one embodiment of components of a surgical system in accordance with the principles of the present disclosure.
Figure 12:
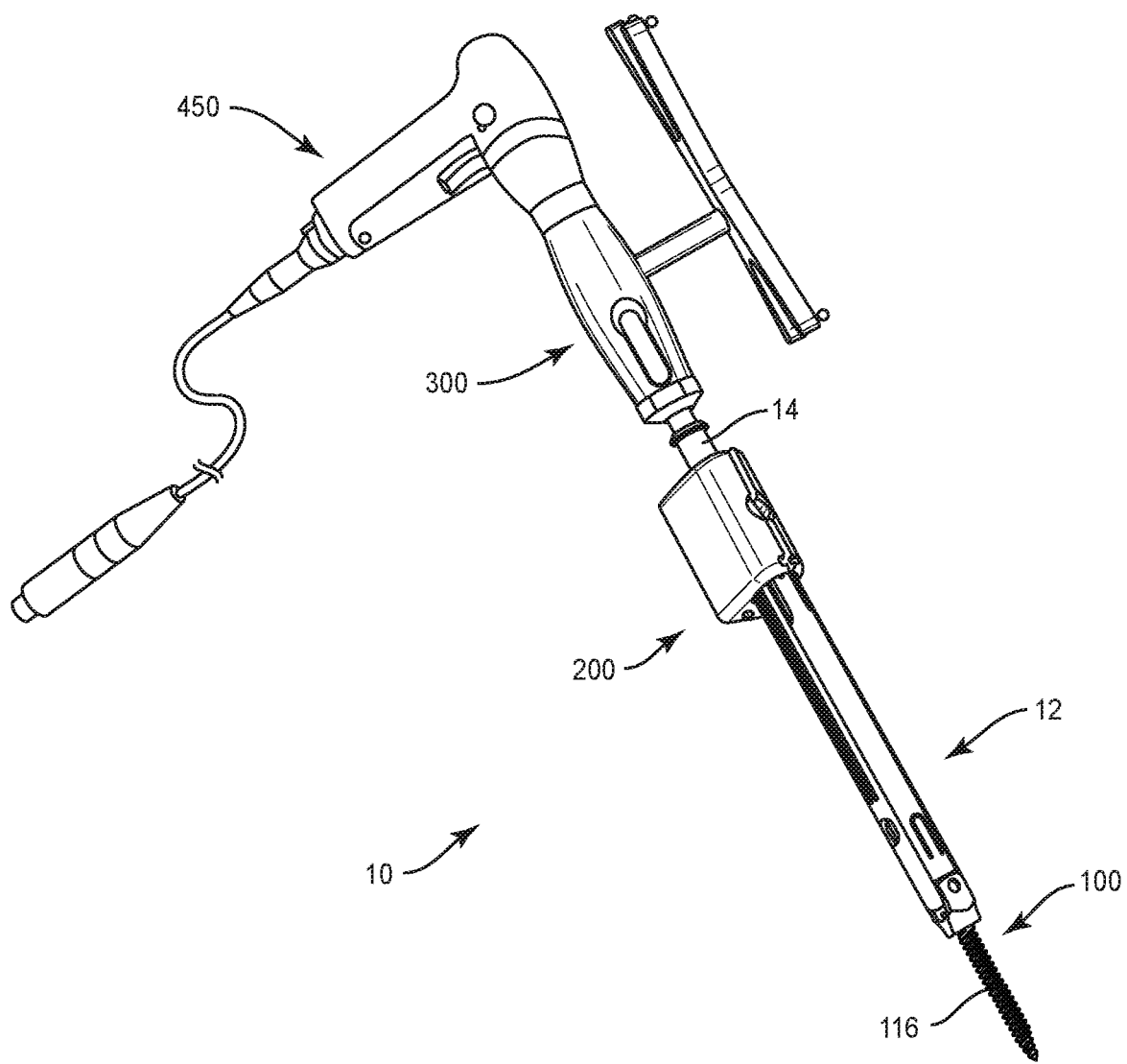
FIG. 12 is a perspective view of one embodiment of components of a surgical system in accordance with the principles of the present disclosure.

Navigation component 300 includes a collar 406 having an inner surface 408 and an outer surface 410. Surface 408 defines a passageway 412. Surface 408 is configured for releasable engagement with part 58, as discussed herein. Passageway 412 is configured to receive part 58. Surface 408 defines a lock, such as, for example, at least one resilient prong or tab 414. In one embodiment, collar 406 includes a plurality of tabs 414, as shown in FIG. 10. Each tab 414 includes an inner surface 416 that defines a cutout 418 and an outer surface 420. Each cutout 418 includes raised portions 422 that define edges of cutout 418. Cutout 418 is configured to receive flange 80, In its initial position, surface 420 is aligned with surface 410 of collar 406.

Navigation component 300 is connected with adaptor 250 and driver 12, as discussed herein. To connect navigation component 300 with adaptor 250 and driver 12, collar 406 is translated over a shaft 252 of adaptor 250, in the direction shown by arrow B in FIG. 6, such that flange 80 engages portions 422 and applies a force to tabs 414 to move tabs 414 outwardly, in the direction shown by arrows C in FIG. 10, such that surface 420 is deflected from surface 410. As flange 80 translates over portions 422, flange 80 moves into cutouts 418 allowing tabs 414 to move back to their initial position. In some embodiments, navigation component 300 is configured for removable engagement with adaptor 250 and driver 12. In some embodiments, navigation component 300 may be integrally formed with adaptor 250 and/or driver 12. In one embodiment, flange 82 is configured to engage collar 406 to reduce vibrations resulting from the torque of an actuator, such as, for example, actuator 450.

Driver 12 is configured for use with end effector 200 of robotic arm R. End effector 200 includes a surface 202 that defines a cavity, such as, for example, a channel 204. Channel 204 is configured for passage of bone fastener assembly 150 and disposal of driver 12. Robotic arm R includes position sensors (not shown), similar to those referenced herein, which measure, sample, capture and/or identify positional data points of end effector 200 in three dimensional space for a guide-wireless insertion of bone fasteners 100 with selected vertebral levels. In some embodiments, the position sensors of robotic arm R are employed in connection with surgical navigation system 306 to measure, sample, capture and/or identify positional data points of end effector 200 in connection with surgical treatment, as described herein. The position sensors are mounted with robotic arm R and calibrated to measure positional data points of end effector 200 in three dimensional space, which are communicated to computer 308. In some embodiments, effector 200 is connected with driver 12 after navigation component 300 is connected with adaptor 250 and driver 12. In some embodiments, effector 200 is connected with driver 12 before navigation component 300 is connected with adaptor 250 and driver 12.

In assembly, operation and use, spinal implant system 10, similar to the systems and methods described herein, is employed with a surgical procedure, such as, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In use, to treat vertebrae (not shown), a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of the vertebrae as well as for aspiration and irrigation of a surgical region.

Pilot holes (not shown) are made in selected levels of vertebrae for receiving bone fasteners 100, Bone fastener assembly 150 is connected with driver 12, as described herein. Drive 22 is engaged with socket 110 and screw 64 is disposed in a non-locking configuration, as described herein, such that screw 64 is freely translatable relative to inner shaft 56 within channel 52 and rotatable relative to outer sleeve 14. With bone fastener assembly 150 connected with outer sleeve 14, handle 90 is manipulated for rotation such that inner shaft 56 rotates screw 64 relative to and independent of outer sleeve 14, as described herein. Threaded engagement of screw 64 and receiver 102 pulls and/or draws bone fastener 100 into the locking configuration with driver 12 for releasable fixation therebetween.

Handle 90 is removed from driver 12 and adaptor 250 is connected with driver 12, as described herein. Navigation component 300 is connected with driver 12, as described herein. Driver 12, connected with bone fastener assembly 150, is oriented for disposal with end effector 200 of robotic arm R, as described herein. The assembly of driver 12/bone fastener assembly 150 are disposed with channel 204 for implantation of bone fasteners 100 with vertebrae employing robotic arm R and/or surgical navigation system 306, as described herein. Actuator 450 is connected with shaft 252 and drive 22 engages bone fastener 100, as described herein, and outer sleeve 14 is rotated to drive, torque, insert or otherwise connect bone fastener 100 with adjacent tissue. Screw 64 remains releasably fixed with receiver 102, independent of outer sleeve 14 rotation and/or engagement or friction with end effector 200 to resist and/or prevent disengagement or unthreading of screw 64 from receiver 102. In some embodiments, driver 12 is manipulated to deliver one or more bone fasteners 100 to a surgical site including vertebrae. Sensor array 302 receives signals from navigation component 300 to provide a three-dimensional spatial position and/or a trajectory of the assembly of driver 12/bone fastener assembly 150, which may be disposed with end effector 200, relative to vertebrae and/or components of spinal implant system 10 for display on monitor 310.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 14-18, spinal implant system 10, similar to the systems and methods described herein, includes a driver 612, similar to driver 12 described herein. Driver 612 includes a tubular outer sleeve 614, similar to sleeve 14 described herein. Outer sleeve 614 includes a surface 650 that defines a channel 652. Channel 652 is configured for disposal of an inner shaft 656 and a screw 664 described herein. End 620 of outer sleeve 614 includes a drive 622, similar to drive 22 described herein. Drive 622 includes a surface 624 that defines a channel 626 such that drive 622 is cannulated.

Driver 612 includes a part 658, similar to part 58 described herein, disposed with sleeve 614. Part 658 is connectable with a surgical instrument, such as, for example, a bone cement delivery device 700. Part 658 has a flange 680 and a flange 682 that is spaced apart from flange 680 by a recess 684. Part 658 has a surface 686 that defines a cavity 688 configured for attachment with bone cement delivery device 700.

Figure 17:
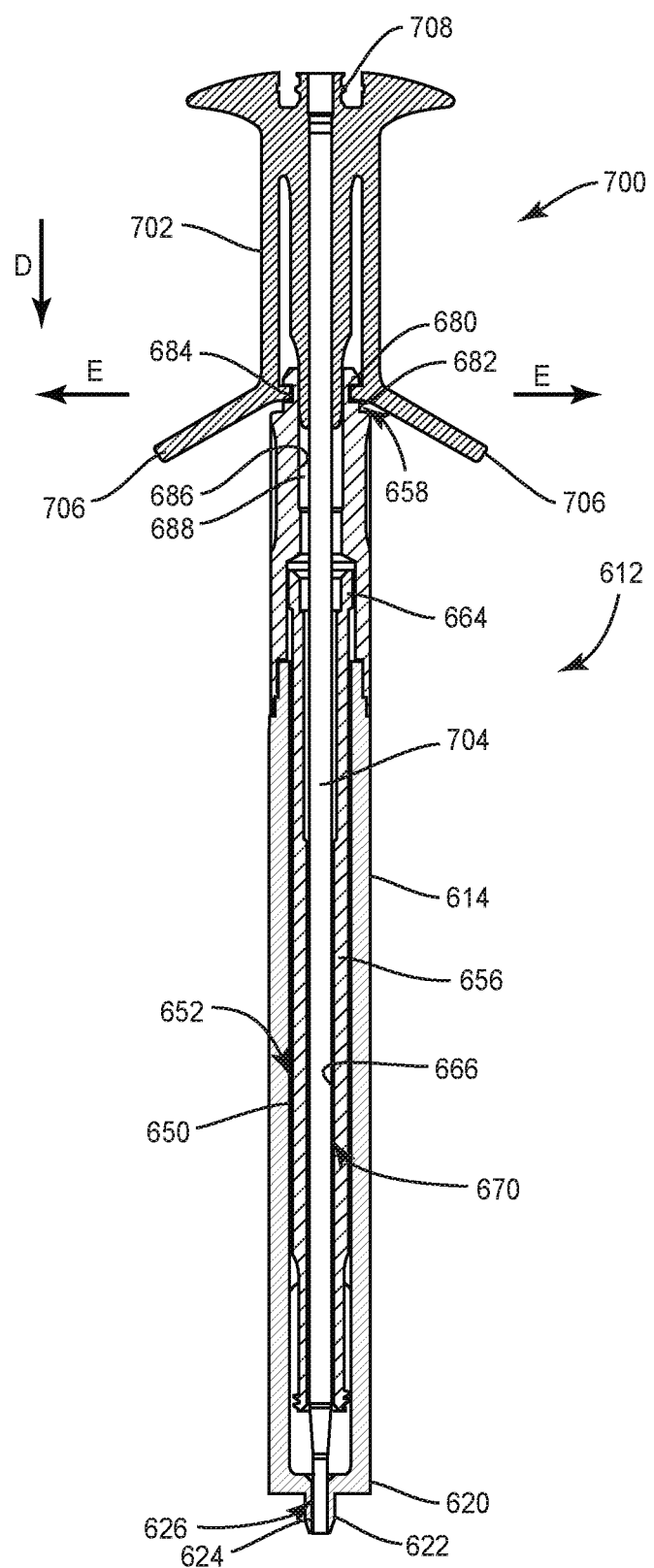
FIG. 17 is a side cross section view of one embodiment of components of a surgical system in accordance with the principles of the present disclosure.

Inner shaft 656 includes a surface 666 that defines a passageway 670. Passageway 670 extends along inner shaft 656 forming a cannulated inner shaft 656. Passageway 670 is disposed in communication with channel 626 such that bone cement delivery device 700 extends through an entire length of driver 612, as shown in FIG. 17. Inner shaft 656 is configured for disposal of bone cement delivery device 700. Bone cement delivery device 700 is configured to deliver bone cement to a surgical site and/or bone fastener 100, as described herein.

Bone cement delivery device 700 includes a handle 702 and a shaft 704. Handle 702 is configured for connection with driver 612. Handle 702 includes a pair of spring arms 706. Arms 706 are configured for a snap fit connection with part 658. Arms 706 each include a protrusion 710. Protrusions 706 are configured to facilitate connection of bone cement delivery device 700 with driver 612. For example, handle 702 is manipulated for disposal with driver 612. Arms 706 are disposed adjacent part 658. Protrusions 710 are disposed in an initial orientation. Handle 702 is translated, in a direction shown by arrow D in FIG. 17. As protrusions 710 translate over flange 680, protrusions 710 are deflected outward, in a direction shown by arrows E in FIG. 17, into a second, expanded orientation. As protrusions 710 translate over flange 780 into recess 684, protrusions 710 are resiliently biased, for example, snap back to the initial orientation for disposal with recess 684. Flanges 680, 682 resist and/or prevent handle 702 from disengaging from part 658 by capturing protrusions 710 within recess 684. Bone cement delivery device 700 is configured for removable engagement with driver 612.

Handle 702 includes a mating surface 708 configured for connection with a bone cement source (not shown). Shaft 704 extends through handle 702 for communication with the bone cement source. In some embodiments, the bone cement source can include a syringe or a pump including a port for connection with a source of bone cement. In some embodiments, the bone cement may include a poly(methyl methacrylate) (PMMA); methyl methacrylate (MMA); calcium phosphate; a resorbable polymer, such as, for example, PLA, PGA or combinations thereof; a resorbable polymer with allograft, such as, for example, particles or fibers of mineralized bone and/or combinations thereof.

Figure 18:
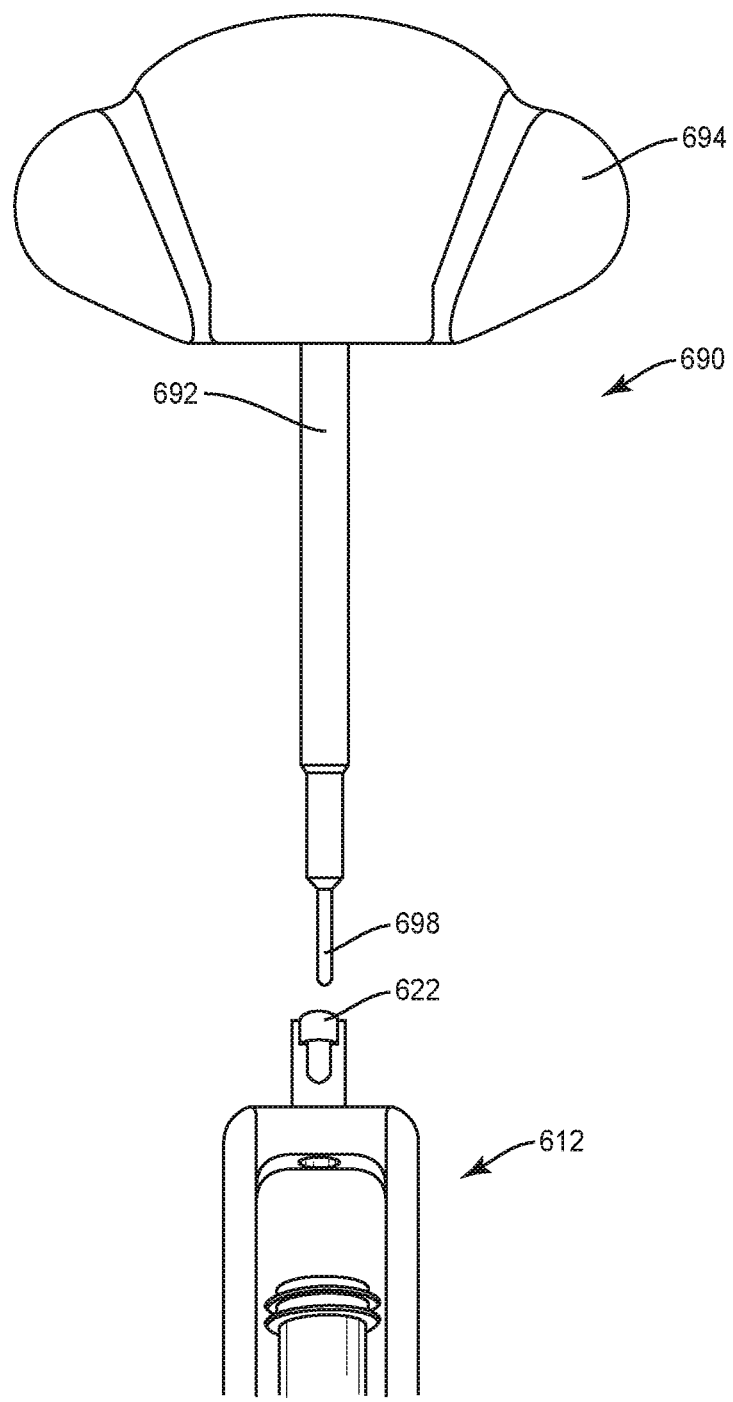
FIG. 18 is a side view of components of one embodiment of a surgical system in accordance with the principles of the present disclosure.

In some embodiments, driver 612 includes a handle 690, similar to handle 90 described herein, as shown in FIG. 18. Handle 690 is configured to actuate rotation of inner shaft 656 and screw 664, as described herein. Handle 690 includes a shaft 692 and a gripping portion 694 that is connected with shaft 692. In some embodiments, gripping portion 694 includes curved portions for an ergonomic configuration. Shaft 692 extends through part 658 such that shaft 692 is rotatable relative to part 658. In some embodiments, a distal end of handle 690 includes a punch 698, similar to punch 98 described herein. Punch 698 has a maximum diameter that is less than a maximum diameter of shaft 692 and/or channel 626 of drive 622. Punch 698 is inserted into channel 626 of drive 622 to dislodge material, such as, for example, cement that may trapped in channel 626 of drive 622.

Figure 14:
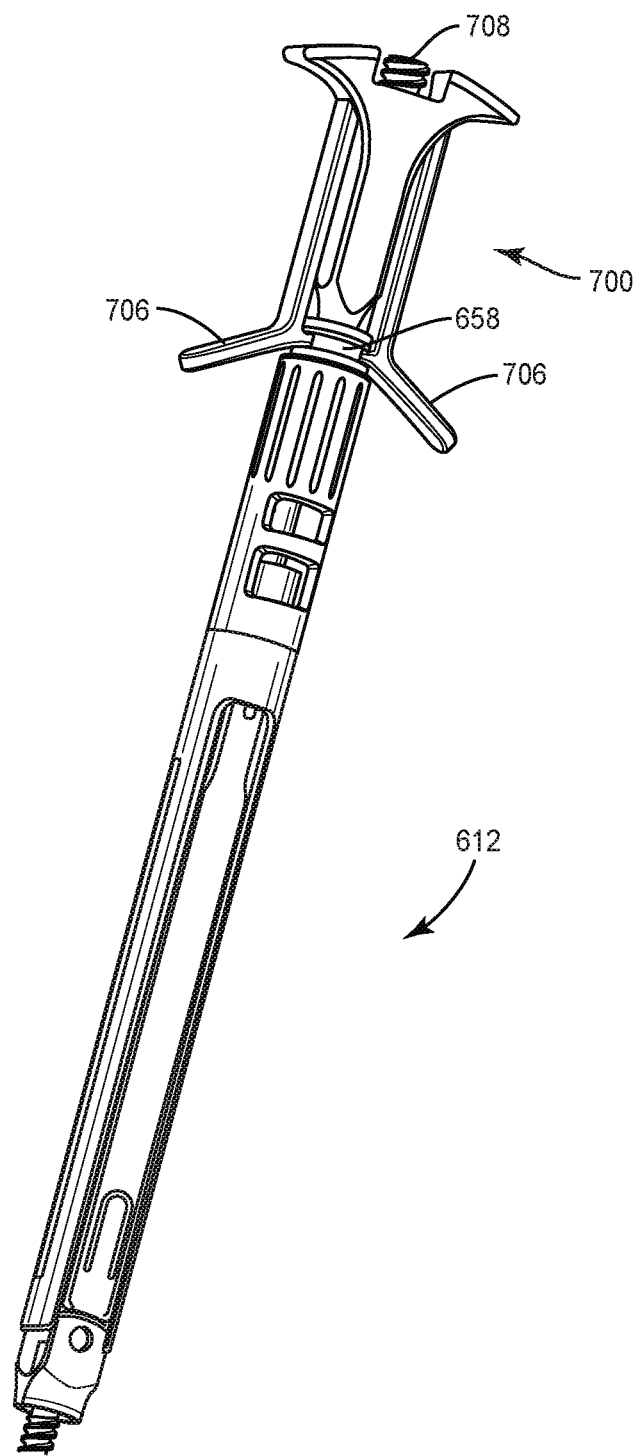
FIG. 14 is a perspective view of components of one embodiment of a surgical system in accordance with the principles of the present disclosure.
Figure 15:
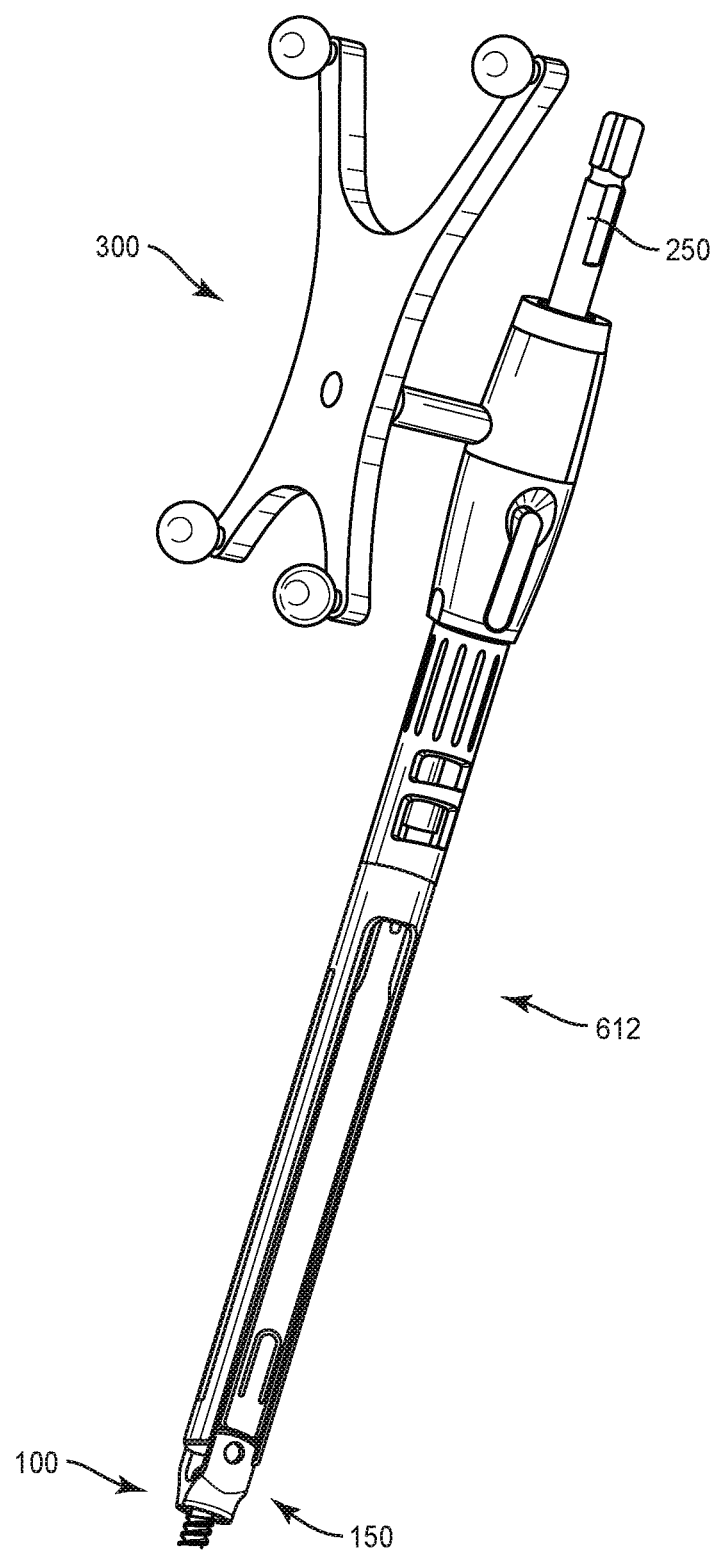
FIG. 15 is a perspective view of one embodiment of components of a surgical system in accordance with the principles of the present disclosure.
Figure 16:
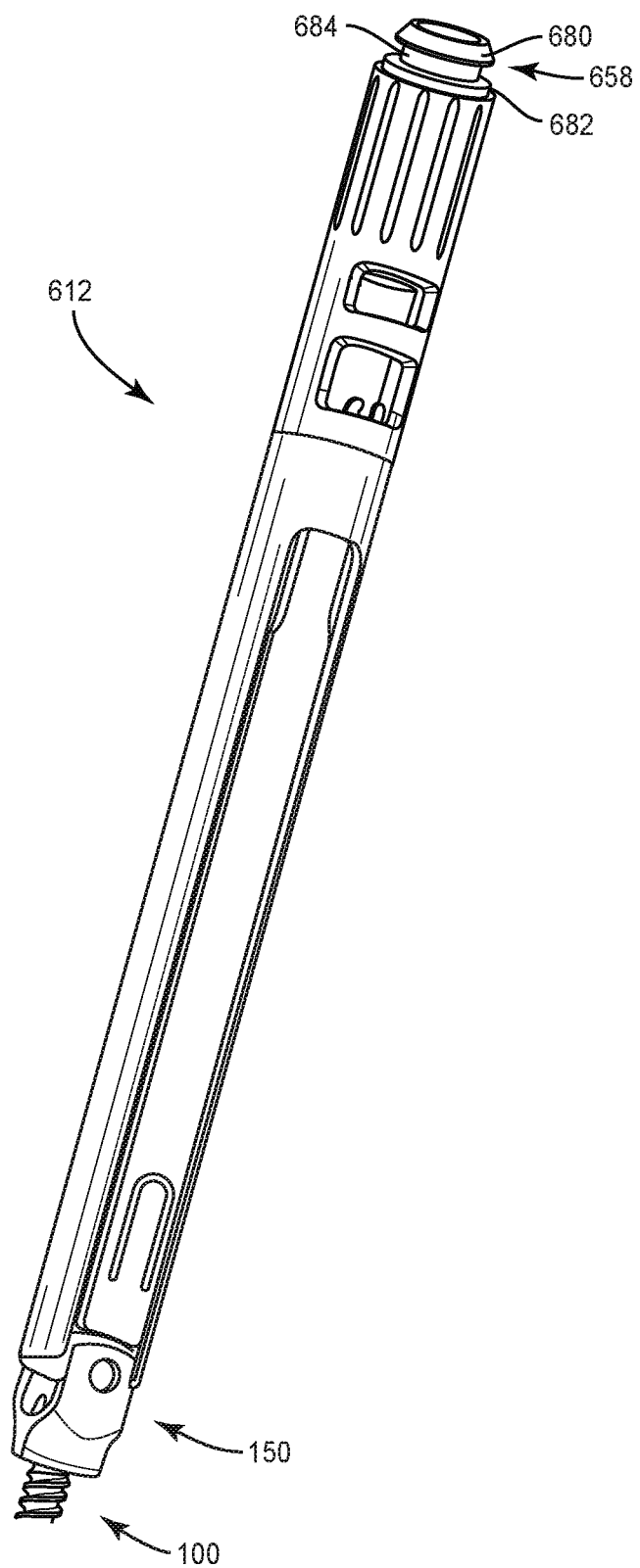
FIG. 16 is a perspective view of one embodiment of components of a surgical system in accordance with the principles of the present disclosure.

In use, bone fastener 100 is engaged with tissue, as described herein, utilizing adaptor 250 and navigation component 300, as shown in FIG. 15. Adaptor 250 and navigation component 300 are disengaged from driver 612 and driver 612 remains engaged with bone fastener 100 and vertebrae, as shown in FIG. 16. Bone cement delivery device 700 is engaged with driver 612 such that shaft 704 is disposed with passageway 670 and channel 626, as shown in FIGS. 14 and 17. Arms 706 are engaged with part 658, as described herein. Cement is delivered through shaft 704 for disposal with bone fastener 100.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member including a drive engageable with a first mating surface of a bone fastener, the first member comprising an inner surface defining a channel, the first member including an outer sleeve having a maximum length defined by a distance from a proximal end surface to an opposite distal end surface, the drive protruding distally from the distal end surface, the drive being located radially inward relative to the inner surface;

a second member defining a central longitudinal axis, the second member being positioned in the channel such that the central longitudinal axis intersects the drive and the second member is rotatable relative to the first member, the second member including an engagement element connectable with a second mating surface of the bone fastener; and a part disposed with the first member and being alternately connectable with an actuator and an adaptor attachable with an image guide.

2. A surgical instrument as recited in claim 1, wherein the actuator includes a removable handle.

3. A surgical instrument as recited in claim 1, wherein the actuator includes a handle and a distal end including a punch.

4. A surgical instrument as recited in claim 1, wherein the actuator is rotatable relative to the part.

5. A surgical instrument as recited in claim 1, wherein the actuator extends through the part to engage the second member.

6. A surgical instrument as recited in claim 1, wherein the actuator engages the second member for rotation therewith.

7. A surgical instrument as recited in claim 1, wherein the part is separate and connectable with the first member, the part including an inner surface that defines an axial cavity.

8. A surgical instrument as recited in claim 1, wherein the surgical instrument includes a bone filler device.

9. A surgical instrument as recited in claim 1, wherein the engagement element includes a screw having an outer thread surface connectable with the second mating surface.

10. A surgical instrument as recited in claim 1, wherein the drive is integrally connected with the first member.

11. A surgical instrument as recited in claim 1, wherein the drive comprises a distal tip of the first member and the first mating surface includes a drive socket of a bone fastener shaft.

12. A surgical instrument as recited in claim 1, wherein the first member includes a wall surface connectable with an implant support that captures a receiver of the bone fastener having the second mating surface and the wall surface defines a pocket surface engageable with proximal spring tips of the implant support.

13. A surgical instrument as recited in claim 1, wherein the image guide includes a lock engageable with the adaptor.

14. A surgical instrument as recited in claim 1, wherein the image guide includes an emitter configured to generate a signal representative of the position of the surgical instrument.

15. A spinal implant system comprising:
a surgical instrument including an outer sleeve having a drive engageable with a bone fastener shaft, the outer sleeve defining a channel, the surgical instrument including an inner sleeve defining a channel and a central longitudinal axis, the inner sleeve being positioned in the channel such that the central longitudinal axis intersects the drive and the inner sleeve is rotatable relative to the outer sleeve, the outer sleeve having a maximum length defined by a distance from a proximal end surface to an opposite distal end surface, the drive protruding distally from the distal end surface, the drive being located radially inward relative to the inner surface, the inner sleeve including an element connectable with a threaded surface of a bone fastener receiver;

a part disposed with the outer sleeve;

a removable handle being connectable with the part and engageable with the inner sleeve for rotation therewith;

an adaptor being connectable with the part; and an image guide attachable with the adaptor and oriented relative to a sensor to communicate a signal representative of a position of the surgical instrument.

16. A spinal implant system as recited in claim 15, wherein the part includes a mating surface being alternately connectable with the handle and the adaptor.

17. A spinal implant system comprising:
a surgical instrument including an outer sleeve having a drive engageable with a bone fastener shaft, the outer sleeve including an inner surface defining a channel and a central longitudinal axis, the outer sleeve having a maximum length defined by a distance from a proximal end surface to an opposite distal end surface, the drive protruding distally from the distal end surface, the drive being located radially inward relative to the inner surface, an inner sleeve being positioned in the channel such that the central longitudinal axis intersects the drive and the inner sleeve is rotatable relative to the outer sleeve, the inner sleeve including an element connectable with a threaded surface of a bone fastener receiver;

a part disposed with the first member and being alternately connectable with an actuator and an adaptor; and a guide member including an inner surface that defines a cavity configured for disposal of the outer sleeve and an image guide attachable with the adaptor and being oriented relative to a sensor to communicate a signal representative of a position of the guide member.

18. A spinal implant system as recited in claim 17, wherein the guide member includes an end effector of a robotic arm.

19. A spinal implant system as recited in claim 17, further comprising a tracking device including a sensor that receives the signal and communicates with a processor to generate data for display of an image from a monitor, the image representing position of the guide member relative to tissue.

* * * * *